United States Patent

Bacigalupo et al.

[11] Patent Number: 5,837,882
[45] Date of Patent: Nov. 17, 1998

[54] STATIONARY ELEMENT ROLLING CONTACT FATIGUE TESTER

[75] Inventors: Nelson Bacigalupo, Ann Arbor; Douglas Glover, Suttons Bay; Mary-Jo Liston, Whitmore Lake; Robert W. Frayer, Jr., Gregory; James Tisch, Brighton; Leontios Res, Ann Arbor; James Fidler, Grass Lake, all of Mich.

[73] Assignee: NTN Corporation, Osaka, Japan

[21] Appl. No.: 869,767

[22] Filed: Jun. 5, 1997

[51] Int. Cl.⁶ .................................................. G01N 3/56
[52] U.S. Cl. ........................................... 73/7; 73/781
[58] Field of Search ..................... 73/7, 781, 862.541

[56] References Cited

U.S. PATENT DOCUMENTS

| | | | |
|---|---|---|---|
| 3,600,931 | 8/1971 | Bartel | 73/7 |
| 4,452,065 | 6/1984 | Minter. | |
| 4,459,842 | 7/1984 | Kihara et al. | 73/7 |
| 4,914,958 | 4/1990 | Van Damme | 73/7 |
| 5,140,849 | 8/1992 | Fujita et al. | 73/862.541 |

*Primary Examiner*—Max H. Noori
*Attorney, Agent, or Firm*—Harness, Dickey & Pierce P.L.C.

[57] ABSTRACT

An assembly for testing the rolling contact fatigue of a test element for evaluating the differences in the fatigue life between like materials manufactured by different manufacturers or the fatigue life of different bearing materials, heat treatments, surface coatings, lubricants, operating variables, etc. The assembly is configured to rotate load balls around a track in contact with a stationary test element. By allowing the test element to remain stationary during the test, sensors can be installed directly onto or into the element. It is possible to configure the present assembly so that sensors may be placed within millimeters of the rolling contact test track effectively eliminating outside noise and error signals and increasing the accuracy of the sensor measurements. The stationary mounting of the test element also facilitates control of the temperature of the element. In addition, studies of crack initiation and propagation rates on a scale not possible before and the study of the delamination of surface coating would be made possible with the present invention.

21 Claims, 3 Drawing Sheets

STATIONARY ELEMENT ROLLING CONTACT FATIGUE TESTER

BACKGROUND OF THE INVENTION

1. Field of the Invention

The present invention relates to an assembly for testing materials, coatings, heat treatment, lubricants, contact geometry and other parameters of an element under rolling contact stresses. More particularly, the present invention relates to a rolling contact tester in which the test element remains stationary during testing.

2. Background Information

Rolling contact fatigue (RCF) element testers are widely used for evaluating material of the type for manufacturing bearings or other parts subject to rolling contact with adjoining parts. RCF element testers can easily and inexpensively discern the differences in the fatigue life between like materials manufactured by different manufacturers or the fatigue life of different materials, heat treatments, surface coatings, etc.

In order to determine which of several material compositions, material processes, lubricants or other parameters is best suited for a particular use as, for example, a rolling element bearing component, an element is subjected to rolling contact at a known pressure or force within a test instrument. The rolling contact fatigue life is determined from the initiation of the test to the time the element fails, i.e., until the test instrument indicates that the element has succumbed to fatigue or other type of failure. Several elements may be tested and their lives compared to determine which element is best suited for a particular use.

Full scale bearing tests in the application constitute the ultimate proof of a bearing system, but these tests are expensive and time consuming. A more effective and expedient way to study new materials or new processes, which are believed to enhance the fatigue life of materials, is to use an RCF element tester for subjecting a test element of simple geometry to rolling contact fatigue before more expensive and lengthy full bearing tests are conducted.

The prior art RCF test instruments have been limited in their ability to fully and efficiently accumulate and evaluate important failure life information. Prior art testers have an inherent limitation which prohibits sensors from being attached directly to the test element. U.S. Pat. No. 4,452,065, issued Jun. 5, 1984, to Minter is one example of a prior art tester.

The Minter tester provides a test instrument which is simple in concept and design and includes means for insuring that the test element fails due to rolling contact before other load carrying elements in the system. Tests are performed by placing a set of load balls in contact with the test element and rotating the test element with a drive motor. A vibration sensor attached to a bolt of the tester assembly and indirectly to the test element is used to measure vibration changes. The vibration changes can be evaluated to determine the failure life of the test element. Sample studies, conducted on the Minter tester, are restricted to having failures inspected only after the completion of the test. Direct monitoring of the test element with thermocouples or other sensors (i.e. acoustic emission, vibration) during testing cannot be done in a convenient manner since the test element is not stationary. Moreover, the temperature of the element cannot be readily controlled as a means of evaluating the effect of temperature on failure.

Thus, there is a need for an improved RCF test assembly in which the test element remains stationary. There is also a need for an improved RCF test assembly in which test sensors can be attached directly onto or inside of the test element and which also permits control over element temperature. There is a further need for an improved RCF test assembly which can perform multiple tests on a single test element. There is a still further need for an improved RCF test assembly which allows for easy access to the test element and which can be setup for a test in an easy and efficient manner.

SUMMARY OF THE INVENTION

The present invention provides a stationary test element rolling contact fatigue test assembly. The test assembly is configured to rotate load balls, in contact with a stationary test element, around the element via loading cups. The rotating load balls carry or transfer a cyclic contact stress onto the test element. This stationary element RCF tester allows sensors to be connected directly on or inside the test element. For example, a sensor or thermocouple can be simply glued or held with a magnet on the test element. A sensor can also be placed inside the element by drilling a hole through the center of the test element. This allows a sensor to be directly attached and within millimeters of the rolling contact area. With this configuration, vibration, temperature, acoustic emissions and other signals suffer only a minimal amount of signal variation from extraneous noise or heat dissipation. The proximity of the sensors to the rolling contact area allows for studies of crack initiation and propagation rates on a scale not possible before. In addition, the study of the delamination of surface coatings is also possible. The stationary element also allows its temperature to be easily controlled.

As well as providing a tester in which the test element remains stationary, the present invention also allows changes in speed, contact stress, temperature and lubrication. The stationary element RCF tester of the present invention offers versatility to change rolling contact fatigue variables. Loading can be applied by hydraulic cylinders, via polymer or steel rings or other mechanical pressing devices. The system can be set up to perform one or more tests on a single test element. The tester is also configured for easy access to the test element and load balls. Setting up for a test run can be done by simply removing the top plate. The test element and load balls (with retainer) can be changed in minutes.

Further objects, features and advantages of the invention will become apparent from a consideration of the following description and the appended claims when taken in connection with the accompanying drawings.

DETAILED DESCRIPTION OF THE PREFERRED EMBODIMENT

Preferred embodiments of the stationary element, rotating load, rolling contact fatigue test assembly of the present invention are described herebelow with reference to the drawings.

Figure 1:
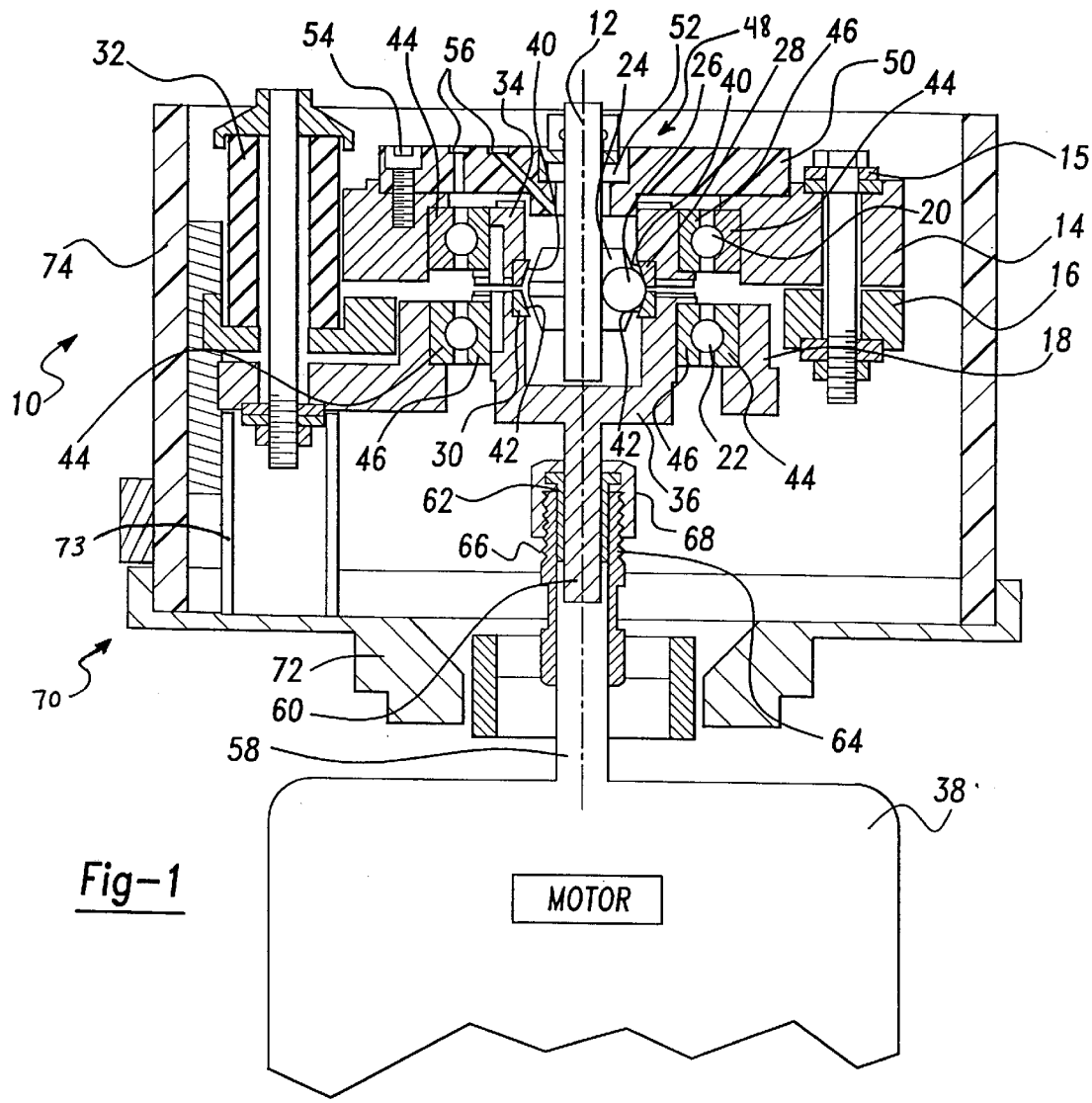
FIG. 1 is a cross-sectional view of the improved rolling contact fatigue tester of the present invention.
Figure 2:
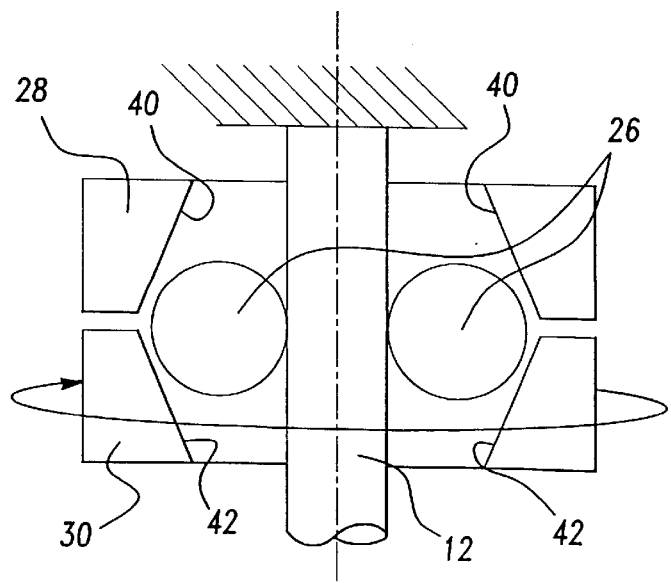
FIG. 2 is an exploded cross-sectional view of FIG. 1 showing the test element, load balls and tapered bearing cup of the present invention.
Figure 3:
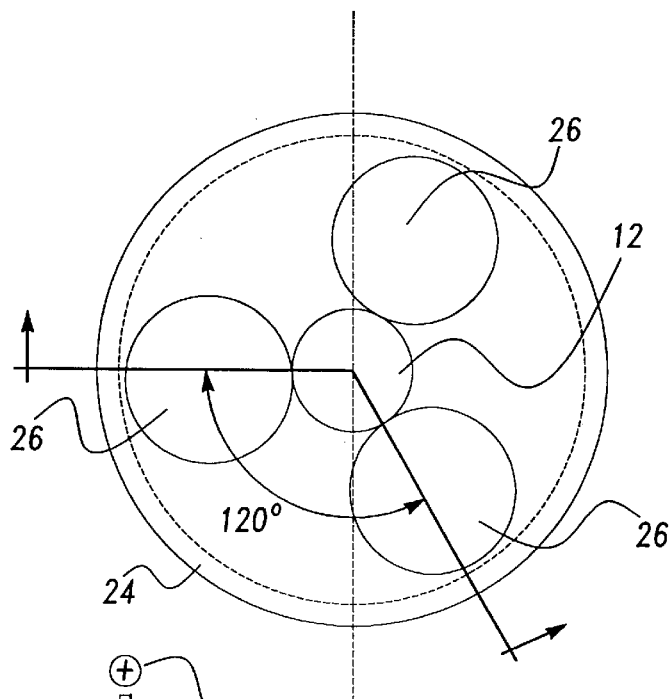
FIG. 3 is a top view of the test element, load balls and retainer of the present invention.

Referring to FIGS. 1, 2 and 3, the preferred embodiment of the RCF tester, is shown generally at 10. The tester 10 comprises three plates, including a top plate 14, a middle plate 16 and a bottom plate 18, two positioning angular bearings, including a top bearing 20 and a bottom bearing 22, a retainer 24, three load balls 26, two tapered bearing cups, including a top cup 28 and a bottom cup 30, a loading mechanism 32, such as a hydraulic or pneumatic press, polymer or steel springs, etc., top and bottom drive housings, 34 and 36 respectively, and a drive motor 38.

The RCF tester, is adapted to subject a test element 12 to cyclical rolling contact fatigue. This is accomplished by urging the load balls 26 against the test element 12 while the load balls 26 are being rotated. As shown in FIG. 1, the load spring 32 is connected between the bottom plate 18 and the middle plate 16, forcing the middle plate 16 toward the bottom plate 18. The middle plate 16 is connected to the top plate 14, by a bolt or other fastener 15. Thus, the middle plate 16 carries the top plate 14 toward the bottom plate 18. The load balls 26 are urged against the test element 12 by wedging action produced by forcing the middle and bottom plates, 16 and 18 respectively, together thereby forcing the top and bottom plates, 14 and 18 respectively, together. The middle and bottom plates, 16 and 18, are forced together by the loading mechanism 32, depicted in the preferred embodiment as a load spring.

Forcing the top and bottom plates, 14 and 18, together causes the top and bottom bearings, 20 and 22, to force the top and bottom drive housings, 34 and 36, to axially urge the top and bottom tapered bearing cups, 28 and 30, toward each other. The top and bottom tapered bearing cups, 28 and 30, include wedge surfaces, 40 and 42, which, when urged together, contact the load balls 26, moving the load balls 26 into engagement with the test element 12.

The top and bottom bearings, 20 and 22, are high precision bearings which are used to guide the tapered bearing cups, 28 and 30, to be centered with respect to the test element 12 in the tester assembly 10. The outer races 44 of the top and bottom bearings, 20 and 22, are pressed into the top and bottom plates, 14 and 18, respectively. The inner races 46 of the top and bottom bearings, 20 and 22, are pressed into the top and bottom drive housings, 34 and 36, respectively.

The RCF tester assembly 10 includes mounting means, indicated generally at 48, for mounting and aligning the test element 12. The test element 12 is in the form of a rod having a length of approximately 3 inches and a diameter of approximately 0.375 inches. The mounting means 48 comprises a cover 50 and an anchoring device 52. The anchoring device 52 is configured to clamp onto the test element 12 to keep the element from rotating and to align the element concentric with the balls. The cover 50, which is attached to the top plate 14 with screws or other fasteners 54, holds the anchoring device 52 and test element 12 in place. The cover 50 can be easily attached or removed to facilitate setup and to allow easy access to the test element 12 and load balls 26. Furthermore, the cover can be configured with lubricant feed cavities 56 for providing lubricant to the bearings or other internal components. The cover can have cavities or be made of a transparent material to allow viewing of the rotating components.

In the preferred embodiment, the load balls 26 comprise three spherical balls disposed symmetrically, that is arranged 120° apart, around the test element 12. The exact number of spherical balls is not critical, however, tests have shown that the use of three or five spherical balls provides stability under test conditions. The load balls 26 are 0.5 inches in diameter and are configured to rotate around the test element 12, in contact with the test element 12, to impose a cyclic stress on the test element 12.

The load balls 26 used with the tester 10 can be made of various materials and with different surface finishes in order to modify the contact stresses or lubrication behavior of the test. The load balls 26 may be roughened by various techniques such as by sand or grit blasting or tumbling.

The top and bottom tapered bearing cups, 28 and 30, are pressed into the inside diameter of the top and bottom drive housings, 34 and 36, respectively. The drive motor 38 is configured to rotatably drive a motor spindle 58 connected to the bottom drive housing 36. The connection between the motor spindle 58 and bottom drive housing 36 is accomplished by inserting a bottom cylindrical section 60 of the bottom drive housing 36 into a segmented first collar member 62 located within a tapered bore of a second collar member 64 having an externally threaded upper portion 66. A lock nut 68 having an internally threaded cup-shaped portion is threaded onto the threaded upper portion 66 of the second collar member 64, forcing the first collar member 62 into the tapered bore of the second collar member 64 to clamp or grip the bottom cylindrical section 60 of the bottom drive housing 36. Therefore, the motor spindle 58 rotates the bottom drive housing 36 which in turn rotates the top drive housing 38 via the load balls 26.

The tapered bearing cups, 28 and 30, rotate with the top and bottom drive housing, 34 and 36, and drive the load balls 26 around a test track on the test element 12 imposing a cyclic stress on the test element 12. In the preferred embodiment, one rotation of the tapered bearing cups, 28 and 30, results in 2.86 stress cycles on the test element 12 (provided that slip does not occur).

Since the test element remains stationary during the test cycle, sensors (not shown) can be easily attached directly onto the test element 12. For example, a sensor or thermocouple can be simply glued to or held with a magnet on the test element 12. A sensor can also be placed inside the test element 12 by drilling a hole through the center of the test element. This would allow the sensor to be within millimeters of the rolling contact test track. Vibration, temperature, acoustic emissions and other signals could be obtained having a minimal amount of noise or heat dissipation. The proximity of the sensors to the rolling contact test track would allow for studies of crack initiation and propagation rates on a scale not possible before. In addition, the study of the delamination of surface coatings would also be possible. Understanding these failure mechanisms would aid research and development of materials and treatment processes with improved fatigue lives.

Support means, indicated generally at 70, can be secured to a table or platform (not shown) by brackets and screws or other similar attachment means for supporting the RCF tester 10 and motor 38. The support means 70 can also include three support tubes 73, or splash guard 74 surrounding the assembly and extending upwardly from the basin 72 of the tester 10. During test runs, lubricant is dripped onto the bearings, 20 and 22, and rotating load balls 26. The splash guard 74 collects lubricant being thrown off the bearings, 20 and 22, and load balls 26 into the basin 72.

The support means 70 further includes vibration dampening means for connecting the support means to the support table and for dampening vibrations therebetween. Thus, external vibrations are absorbed isolating the assembly from external vibrations.

As stated above, the assembly includes top and bottom tapered bearing cups, 28 and 30, having inclined surfaces 40 and 42, which when urged together, contact the load balls 26 moving the load balls 26 into engagement with the test element 12. The inclined surfaces 40, and 42, each define a frustoconical inner race in each bearing cup. The frustoconical inner surfaces of the tapered bearing cups, 28 and 30, are opposed and in wedging engagement with the load balls 26 so that the wedging force applied thereby urges the tapered bearing cups, 28 and 30, together against the load balls 26.

The assembly could include only a single tapered bearing cup having an inclined surface in rolling engagement with the load balls 26. The single bearing cup would be actuated to force the load balls 26 inwardly against the test material 12 while axial movement of the load balls 26 is restrained by a second flat surface.

The load balls 26 are spaced annularly about the test element 12 by the retainer 24. The retainer 24 includes openings spaced annularly thereabout in which the load balls 26 are caged. The openings also allow the load balls 26 to be exposed to the test material element 12 and further provide sufficient space for the slight inward and outward movement of the load balls 26 in response to the wedging action of the tapered bearing cups, 28 and 30. In the event of the use of five load balls, there is no need for the use of the retainer 24.

Figure 4:
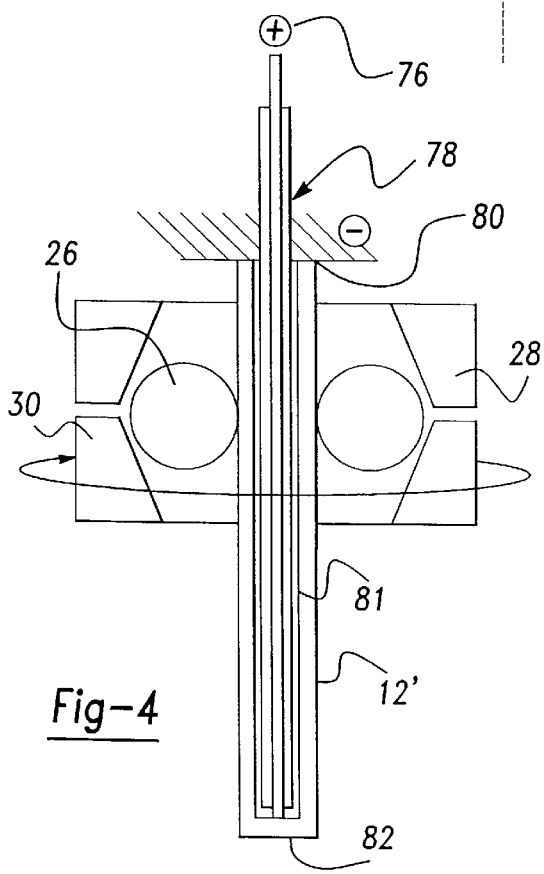
FIG. 4 is a cross-sectional view similar to FIG. 2 showing that the test element, due to it remaining fixed, may be subjected to heating while the tester is operating by passing an electrical current through the element.
Figure 5:
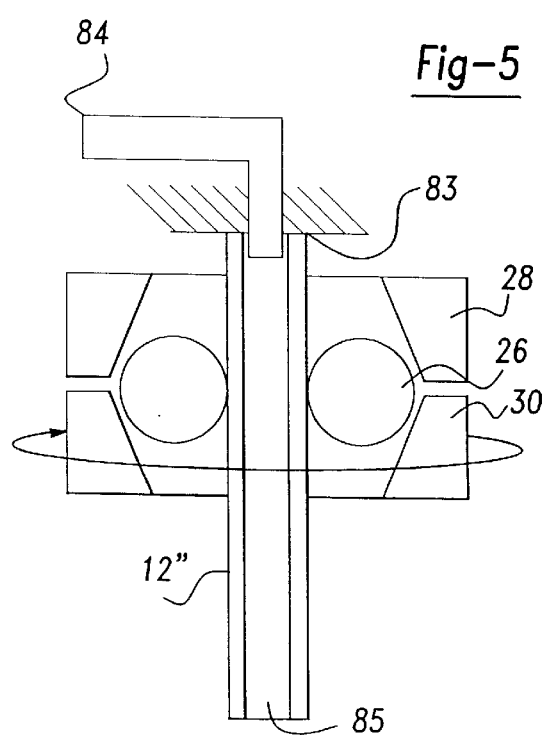
FIG. 5 is a cross-sectional view similar to FIG. 2 showing that the test element, due to the remaining fixed, may be subjected to cooling by passing a cold gas through a passageway formed through the element.

As shown in FIG. 4, since the test element 12 remains stationary during the test cycle using tester 10, the element can also be subjected to heating or cooling during the test. This allows additional studies as to the effects of temperature variations on the life of the test element. In order to heat the element, a hole 81 can be drilled though the center of the element 12'. Then a power supply 76 can provide power to an insulated wire 78 inserted through the center of the element 12'. This supplies current to the non-grounded end of the element 82. As the supplied current then travels back to the grounded end of the element 80, heat is generated by the resistance encountered within the element 12'. This allows the element 12' to be heated without interrupting the test cycle. Likewise, as shown in FIG. 5, to cool the element during the test cycles, the element 12" can again be drilled through the center, creating a channel 85 through which a cooled gas or liquid (such as $N_2$) can flow. A tube 84 can be inserted in the fixed end 83 of the element 12" to allow for the supply of cooled gas or liquid to enter the channel 85, thereby cooling the element 12" while the test continues. Due to the fact that the element is fixed while the load balls 26 rotate about it, either heating or cooling of the element can be achieved without any interruption of the test cycles.

Figure 6:
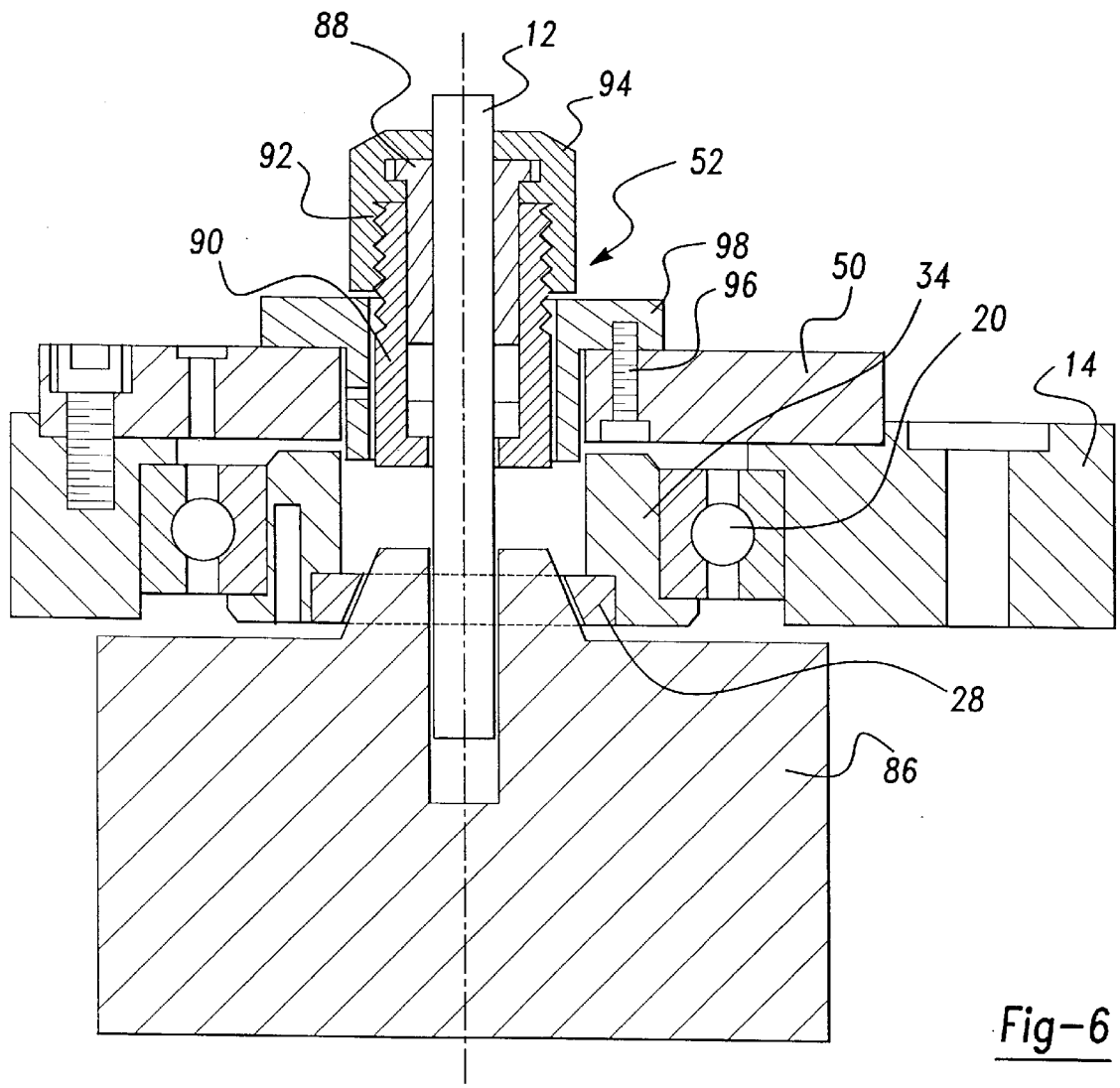
FIG. 6 is a cross-sectional view of the upper part of the tester showing how an aligning fixture can be used to center the test element while the element is securely fastened in place.

As shown in FIG. 6 the RCF tester assembly 10 includes mounting means, indicated generally at 48, for mounting the test element 12. FIG. 6 shows a detailed mounting assembly 52, including an aligning fixture 86. Prior to securing the element 12 within the mounting means, an aligning fixture 86 can be used to hold the element in its proper location. This ensures that the element 12 will be concentric with the rotating parts (top tapered bearing cup 28) as the element is secured to the mounting assembly 52. The mounting assembly 52 comprises of a segmented collar member 88 and a second collar member 90 with an externally threaded upper portion 92, onto which a lock nut 94 is threaded. The anchoring device assembly 52 includes a flanged collar 98 affixed to the second segmented collar member 90, which is secured to the cover 50 by a screw or other fastener 96. The test element 12 is inserted through the first segmented collar member 88, which is forced into the tapered bore of the second collar member 90 as the lock nut 94 is tightened onto the threaded portion of the second collar member 92. All of this is done while the aligning fixture 86 holds the test element 12 in its proper location relative to the rotating parts. This results in the first collar member clamping tightly to the upper end of the test element 12, holding it firmly in place after the aligning fixture 86 is removed. Once the aligning fixture 86 is removed, the top plate 14 can then be attached to the middle plate 16 as described above, It is to be understood that the invention is not limited to the exact construction illustrated and described above, but that various changes and modifications may be made without departing from the spirit and scope of the invention as defined in the following claims.

We claim:

1. An assembly for measuring rolling contact fatigue characteristics of a test element by subjecting the test element to a cyclic contact stress during a test phase, said assembly comprising:

mounting means for holding the test element in said assembly, wherein the test element is held stationary during the test phase;

bearing means configured for rotation around the test element during the test phase for placing the cyclic contact stress upon the test element;

loading means for urging said bearing means against a test track portion of the test element during the test phase at a known pressure placing said bearing means in rotatable engagement with the test element, said loading means having a wedge member disposed adjacent to said bearing means, said wedge member including a first bearing cup member having an inclined surface in rolling engagement with said bearing means a second bearing cup member having an inclined surface in opposed wedging engagement to said first bearing cup member and in rolling engagement with said bearing means, a force-applying means for forcing said inclined surfaces into said bearing means thereby applying a determinable load between said bearing means and the test element wherein said force-applying means forces said first and second bearing cup members together against said bearing means, and said force-applying means further including a first positioning bearing coupled to said first bearing cup member and a second positioning bearing coupled to said second bearing cup member and a load spring acting between said positioning bearings to place a load on said bearing cup members, said positioning bearings coupled to said load spring with said load spring non-rotatable with respect to said mounting means, and rotation means for rotating said bearing means around said test element.

2. The assembly of claim 1, further comprising sensing means directly connected to the test element for measuring the rolling contact fatigue characteristics of the test element during the test phase.

3. An assembly for measuring rolling contact fatigue characteristics of a test element by subjecting the test element to a cyclic contact stress during a test phase, said assembly comprising:

mounting means for holding the test element in said assembly, wherein the test element is held stationary during the test phase;

bearing means configured for rotation around the test element during the test phase for placing the cyclic contact stress upon the test element;

loading means for urging said bearing means against a test track portion of the test element during the test phase at a known pressure placing said bearing means in rotatable engagement with the test element, said loading means including a wedge member disposed adjacent to said bearing means, said wedge member including a first bearing cup member having an inclined surface in rolling engagement with said bearing means, a second bearing cup member having an inclined surface in opposed wedging engagement to said first bearing cup member and in rolling engagement with said bearing means, a force-applying means for forcing said inclined surface into said bearing means thereby applying a determinable load between said bearing means and the test element; wherein said force-applying means forces said first and second bearing cup members together against said bearing means; and said force applying means further having a first plate operable connected to said first bearing cup member; a second plate operably connected to a second bearing cup member; and clamping means configured to urge said first and second plates together thus forcing said first and second bearing cup members together against said bearing means, and rotation means for rotating said bearing means around said test element.

4. The assembly of claim 3 further comprising a first drive housing operably connected to said rotation means, said first drive housing operably connected to said first bearing cup member and configured to rotate with said rotation means thus causing rotation of said first bearing cup member and consequently said bearing means.

5. The assembly of claim 1 wherein said force-applying means further comprises:

a first plate operably connected to said first bearing cup member;

a second plate operably connected to a second bearing cup member; and clamping means configured to urge said first and second plates together thus forcing said first and second bearing cup members together against said bearing means.

6. The assembly of claim 5 wherein said force-applying means further comprises:

a middle plate disposed between said first and second plates, said middle plate operably connected to said first plate; and said load spring operably connected to said middle plate and said second plate wherein said load spring forces said middle plate and said second plate together, said middle plate carrying along said first plate thus forcing said first and second bearing cup members together against said bearing means.

7. The assembly of claim 5 further comprising a first drive housing operably connected to said rotation means, said first drive housing operably connected to said first bearing cup member and configured to rotate with said rotation means thus causing rotation of said first bearing cup member and consequently said bearing means.

8. The assembly of claim 7 further comprising said first positioning bearing member operably connected between said first plate and said first drive housing allowing relative rotation between said first drive housing and said first plate, said first positioning bearing member being configured to guide said first bearing cup member.

9. The assembly of claim 8 further comprising:

a second drive housing operably connected to said second bearing cup member and configured to rotate with said rotation of said bearing means;

said second positioning bearing member operably connected between said second plate and said second drive housing allowing relative rotation between said second drive housing and said second plate, said second positioning bearing member being configured to guide said second drive housing and said second bearing cup member.

10. The assembly of claim 1 wherein said bearing means further comprises:

a plurality of load balls held in place by a retainer wherein said load balls rotatably engage said test element and said load balls and said retainer are configured for rotation around said test element during the test phase.

11. The assembly of claim 10 wherein said plurality of load balls comprises three load balls disposed 120° apart around said retainer.

12. The assembly of claim 10 wherein said plurality of load balls have uniformly roughened outer surfaces for decreasing the life of said test element.

13. The assembly of claim 1 wherein said mounting means further comprises:

a cover plate having a centralized aperture for receiving the test element; and an anchoring device operably connected to said cover plate, said anchoring device configured to clamp the test element in a fixed, non-rotatable position.

14. The assembly of claim 1 wherein said rotation means further comprises:

a drive motor operably connected to said bearing means for rotating said bearing means around the test element.

15. The assembly of claim 2 wherein the test element includes a bore drilled through the center of the test element along the longitudinal axis of the test element with said sensing means being disposed inside of said bore in close proximity to said test track portion.

16. The assembly of claim 1 further comprising vibration dampening means for dampening vibrations between the assembly and a support structure.

17. The assembly of claim 1 further comprising a splash wall extending upwardly from a base portion of the assembly for collecting lubricant thrown from said bearing means during the test phase.

18. The assembly of claim 1 wherein means for controlling the temperature of the test element during a test phase are applied at the mounted end of the test element.

19. The assembly of claim 4 further comprising a first positioning bearing member operably connected between said first plate and said first drive housing allowing relative rotation between said first drive housing and said first plate, said first positioning bearing member being configured to guide said first bearing cup member.

20. The assembly of claim 3 wherein said force-applying means further comprises:

a middle plate disposed between said first and second plates, said middle plate operably connected to said first plate; and a load spring operably connected to said middle plate and said second plate wherein said load spring forces said middle plate and said second plate together, said middle plate carrying along said first plate thus forcing said first and second bearing cup members together against said bearing means.

21. The assembly of claim 19 further comprising:

a second drive housing operably connected to said second bearing cup member and configured to rotate with said rotation of said bearing means; and a second positioning bearing member operably connected between said second plate and said second drive housing allowing relative rotation between said second drive housing and said second plate, said second positioning bearing member being configured to guide said second drive housing and said second bearing cup member.

* * * * *